United States Patent [19]

Estep

[11] 4,386,069

[45] May 31, 1983

[54] ADDITIVE SOLUTION AND METHOD FOR PRESERVING NORMAL RED CELL MORPHOLOGY IN WHOLE BLOOD DURING STORAGE

[75] Inventor: Timothy N. Estep, Lindenhurst, Ill.

[73] Assignee: Baxter Travenol Laboratories, Inc., Deerfield, Ill.

[21] Appl. No.: 326,771

[22] Filed: Dec. 2, 1981

[51] Int. Cl.³ .............................................. A61K 35/14
[52] U.S. Cl. ....................................... 424/101; 435/2; 206/438
[58] Field of Search ............................ 424/101; 435/2

[56] References Cited

U.S. PATENT DOCUMENTS

| | | |
|---|---|---|
| 4,222,379 | 9/1980 | Smith . |
| 4,286,597 | 9/1981 | Gajewski et al. . |
| 4,300,559 | 11/1981 | Gajewski et al. . |
| 4,301,800 | 11/1981 | Collins . |
| 4,326,025 | 4/1982 | Buckles et al. ...................... 424/101 |

OTHER PUBLICATIONS

Little and Rumsby, *Scand. J. Hematol.* (1980), 25, pp. 134–140, copyright 1980.
Little and Rumsby, "Lysis of Erythrocytes from Stored Blood by Phospholipase C", *Bio Chemical Journal*, (1980), vol. 188, pp. 39–46.
Laczko et al., "Discocyte, Echinocyte Reversibility and Blood Stored in CPD Over a Period of 56 Days", *Transfusion*, Jul.–Aug. 1979, pp. 379–388.

*Primary Examiner*—Sam Rosen
*Attorney, Agent, or Firm*—Paul C. Flattery; Daniel D. Ryan

[57] ABSTRACT

An additive solution, which can be dispersed in whole blood to enhance preservation of normal red cell morphology during storage, comprises a fatty ester which includes at least two ester linkages comprising fatty hydrocarbon groups of about four to twelve carbon atoms each. The solution can be introduced into the whole blood either at the outset of the storage period or any time during the period in an amount to provide, after its introduction, a concentration of the fatty ester of between 150 and 3,000 micrograms per milliliter of whole blood. When introduced at the outset of storage, morphological changes in the red cells are significantly retarded during the storage period. When introduced at later stages of storage, the solution serves to rejuvenate a significant percentage of red cells which have undergone morphological changes prior to the introduction of the solution.

30 Claims, 7 Drawing Figures

FIG. 2
MORPHOLOGY OF BLOOD STORED FOR ONE DAY AT 4°C
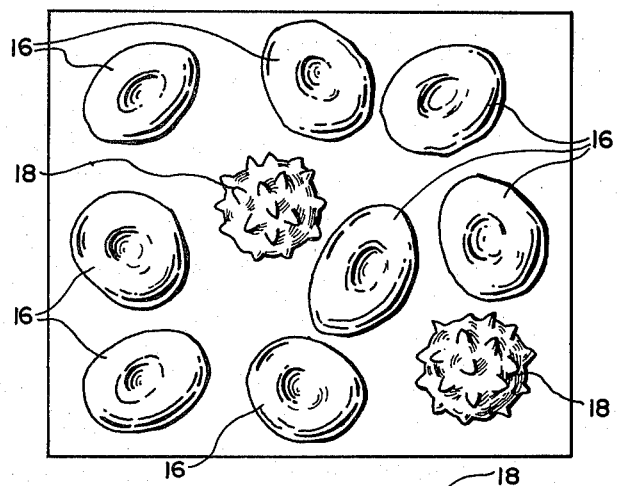
(a) BUFFER CONTROL
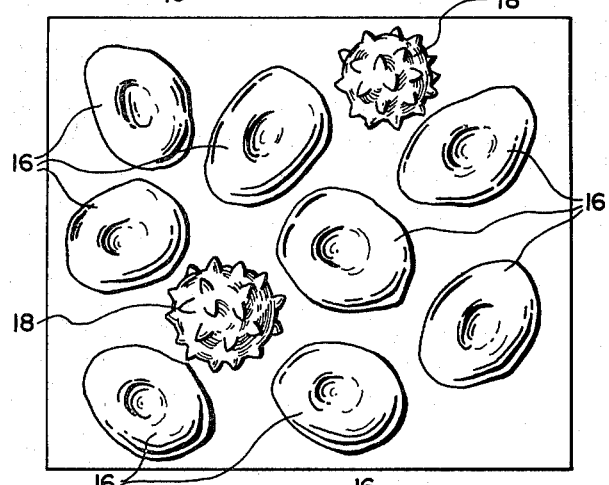
(b) EMULSIFIER CONTROL
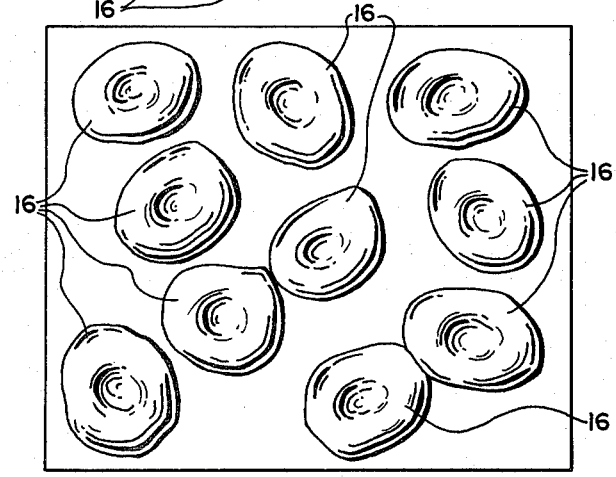
(c) FATTY ESTER EMULSION

MORPHOLOGY OF BLOOD STORED FOR 28 DAYS AT 4°C (a) BUFFER CONTROL (b) EMULSIFIER CONTROL (c) FATTY ESTER EMULSION

RELATIONSHIP BETWEEN DEHP CONCENTRATION AND PLASMA HEMOGLOBIN CONCENTRATION AFTER 21 DAYS AND 35 DAYS OF STORAGE

ADDITIVE SOLUTION AND METHOD FOR PRESERVING NORMAL RED CELL MORPHOLOGY IN WHOLE BLOOD DURING STORAGE

TECHNICAL FIELD OF THE INVENTION

The invention generally relates to methods and materials associated with the storage of whole blood.

DESCRIPTION OF THE PRIOR ART

Whole blood may be collected and stored in the presence of an anticoagulant under conventionally specified conditions for approximately 28 days prior to administration to a patient.

The amount of hemoglobin present in stored blood is known to increase during storage, because, during storage, red blood cells rupture. This phenomenon is generally known as hemolysis. It is desirable, of course, to prevent or minimize hemolysis during storage.

Buckles et al U.S. Pat. No. 4,326,025, the use of emulsions of certain ester materials is disclosed to prevent hemolysis in stored blood. As discussed in the Buckles et al application, the presence of diester materials, such as di-2-ethylhexylphthalate (hereafter called DEHP), or tri-2-ethylhexylphosphate, in stored blood in concentrations of 50 to 100 parts per million has been observed to supress hemolysis.

Also in Smith U.S. Pat. No. 4,222,379, and also in Geissler et al. U.S. Patent Application Ser. No. 105,469 filed Dec. 19, 1979, blood bags plasticized with a diester material, such as DEHP, are shown to reduce the hemolysis of blood therein stored. The DEHP leaches gradually from the walls of the blood bag into the blood and provides a final concentration of DEHP after 21 days of storage of about 30 to 100 micrograms per milliliter of blood.

In addition to hemolysis, it has also been observed that, during storage, red blood cells undergo morphological changes. After even only a few days of storage, a large percentage of the red blood cells lose their normal disc-shaped appearance and develop spicules or crenations. After longer periods of storage, these crenated red cells further assume a generally spherical shape.

It is commonly believed that crenated red cells are capable of regaining their normal disc-shape and organic functions after reinfusion. However, if the red cells have developed the generally spherical shape, it is commonly believed that the red cells have been irreversibly damaged and cannot again regain their normal shape and functions after reinfusion.

Concentrations of the antihemolytic agents on the order disclosed in the above-discussed Buckles Smith Patents do not have a significant effect in reducing morphological changes in the red cells during storage. For example, after exposure to a concentration of as much as 100 micrograms of DEHP per milliliter of whole blood, more than 75 percent of the red cells may still exhibit a crenated morphology after seven days of storage.

Recognizing that it is desirable to return as many morphologically normal red blood cells to the blood stream as possible after storage, it is one of the principal objects of this invention to provide a means for preserving normal red cell morphology in whole blood during storage.

SUMMARY OF THE INVENTION

To achieve this and other objects, the invention provides an additive solution which can be introduced into whole blood to enhance the preservation of normal red cell morphology during storage. The solution comprises a fatty ester which includes at least two ester linkages comprising fatty hydrocarbon groups of about four to twelve carbon atoms each. The solution is introduced into the whole blood in an amount to provide, after its introduction, a concentration of the fatty ester of between 150 and 3,000 micrograms per milliliter of whole blood.

In the preferred embodiment, the fatty ester is dispersed in the whole blood in the form of an emulsion. It is also preferred that the concentration of the fatty ester be generally between 250 and 500 micrograms per milliliter of whole blood.

The additive solution which embodies the features of the invention can be introduced at the very outset of the storage period to retard the formation of morphological changes in the red cells. Alternately, the solution may be introduced into whole blood which has already been stored, with the surprising result that a significant number of the red cells which have undergone morphological changes during the preceeding storage period are rejuvenated and return to their normal form in the presence of the solution.

The invention also provides a method for storing whole blood, which method comprises introducing the above-described fatty ester in the whole blood to achieve a concentration of the fatty ester of between 150 and 3,000 micrograms per milliliter of whole blood.

Other features and advantages of the embodiments of the invention will become apparent upon reviewing the following more detailed description and Examples, the drawings, and the appended claims.

DESCRIPTION OF THE DRAWINGS

FIG. 2 (a), (b), and (c) is a microscopic plan view of whole blood samples stored for one day in the presence of various solutions, one of which embodies the features of the invention;

Before explaining the embodiments of the invention in detail, it is to be understood that the invention is not limited in its application to the details as set forth in the following description, examples, or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENT

Figure 1:
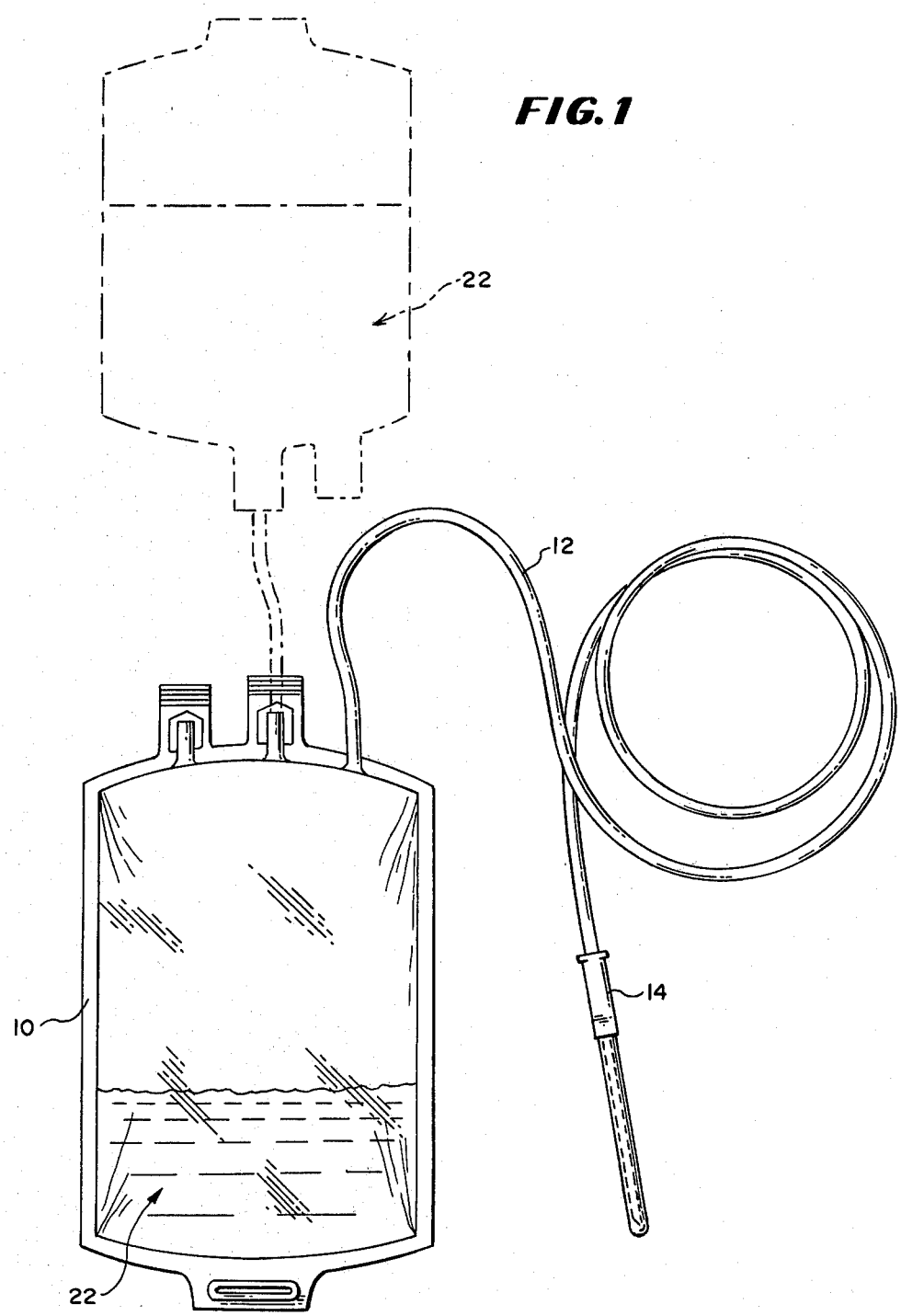
FIG. 1 is a plan view of a blood bag containing a solution which embodies various of the features of the invention.

A blood collection and storage container 10 is shown in FIG. 1. The container 10 is typically made from medical grade polyvinyl chloride plastic, although other plastics, such as a polyolefin, could be utilized. The container 10 includes a donor tube 12 and a phlebotomy needle 14, through which whole blood from a patient or donor is introduced into the container 10 for storage. An anticoagulant solution is carried within the container 10 to prevent the collected whole blood from clotting during the collection procedure and subsequent storage.

Typically, during storage, the whole blood is subjected to a temperature of about 4° C. The storage period typically lasts between 21 and 35 days.

Figure 3:
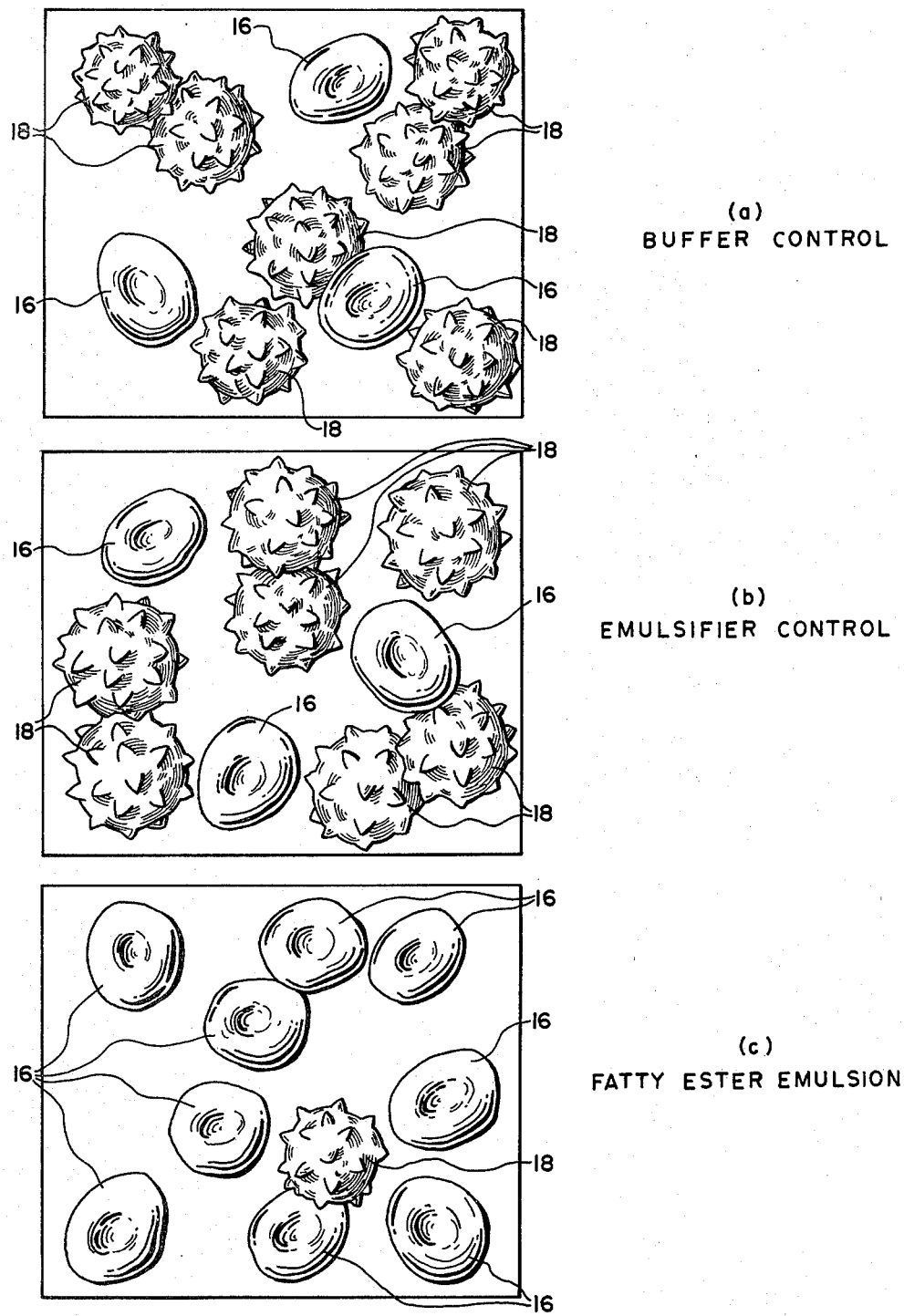
FIG. 3 (a), (b), and (c) is a microscopic plan view of the whole blood samples shown in FIG. 2 after fourteen days of storage.
Figure 4:
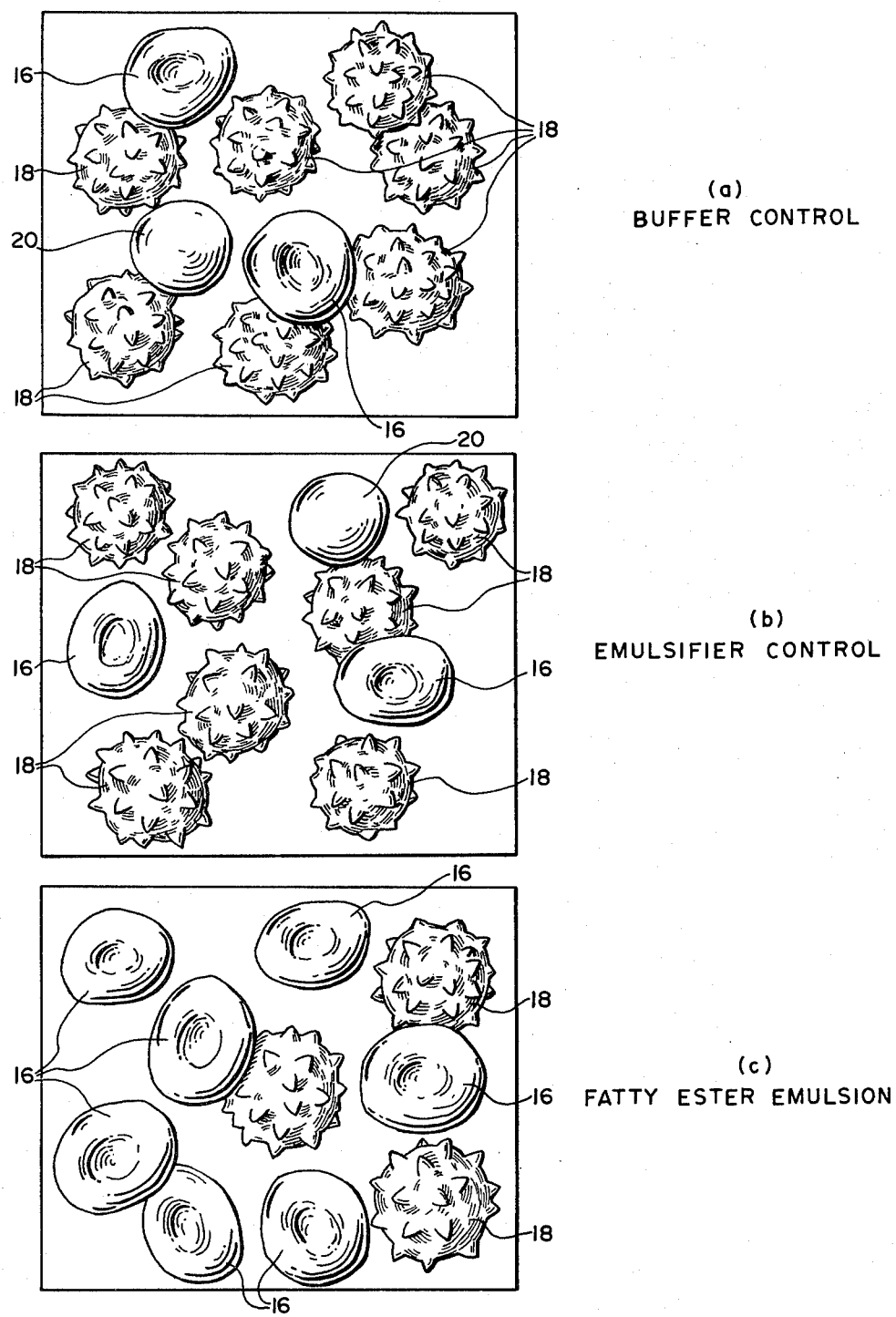
FIG. 4 (a), (b), and (c) is a microscopic plan view of the whole blood samples shown in FIG. 2 after twenty-eight days of storage.

Within the first few days of storage, a great number of red blood cells are observed to undergo an undesirable morphological transition from a normal biconcave disc-shape (shown by the normal red cells 16, or erythrocytes, in FIGS. 2 through 4) to form spicules or crenations (shown by the crenated red cells, or echinocytes, 18 in FIGS. 2 through 4). By the seventh day of storage, the great majority of the red blood (more than 75 percent) will have undergone this undesirable morphological change and display marked spiculation.

During further storage, the crenated red cells 18 further evolve into spiculate spheres (shown by the spherical red cells 20, or spheroechinocytes, in FIG. 4(a)). This morphology is thought to indicate irreversible cell damage and an inability of the red cells so effected to regain their natural functions upon reinfusion.

These undesired morphological changes in the red cells take place even when the whole blood is stored in conventional polyvinyl chloride blood containers plasticized with DEHP, which is known to leach into the whole blood suppress red cell hemolysis during storage.

To preserve red blood cell morphology during the storage period, the invention provides an additive solution which can be introduced into the whole blood stored in the container 10. The additive solution 22 includes a fatty ester containing at least two ester linkages comprising fatty hydrocarbon groups of about four to twelve carbon atoms each. The fatty ester is carried within the solution 22 in an amount sufficient to provide, after the introduction of the solution 22 into the whole blood, a concentration of between 150 and 3,000 micrograms of the fatty ester for each milliliter of whole blood stored in the container 10.

It is believed preferably that the fatty ester be carried within the solution 22 in an amount sufficient to provide a concentration of between 250 and 500 micrograms of the fatty ester per milliliter of whole blood.

The fatty hydrocarbon groups in the ester linkage (e.g., R—OC⁰—) are preferably alkyl radicals of six to twelve carbon atoms. The ester linkages are preferably spaced closer than the 1, 3 relationship, by which is meant is that the ester linkages are preferably bonded to the same or adjacent carbon or other atoms, such as phosphorous. Most preferably, fatty ester linkages which are bonded to adjacent carbon atoms, or the same phosphorous atom, appear to be among the most active in their desired effect upon red cell morphology.

Fatty ester linkages which are separated farther apart on highly mobile hydrocarbon chains, for example linear alkylene chains, forming compounds such as di-2-ethylhexyladipate, can also be active in desirably effecting red cell morphology. Preferably, such linear hydrocarbon chains contain no more than eight carbon atoms, excluding the ester linkage carbon atoms.

Maleate esters and related materials can also be active in their desired effect upon red cell morphology.

It is also preferable that the organic radicals of the ester linkages be alkyl of seven to ten carbon atoms, e.g., octyl groups, for example N-octyl, heptyl, nonyl, decyl, or 2-ethylhexyl. However, other radicals such as hexyl or dodecyl may be used. Also, similar alkenyl radicals such as octenyl, noneyl, or decenyl containing one or more unsaturated linkages may be used.

Specific examples of the fatty ester materials described above include the various dioctylphthalates and dioctyladipates; dihexylphthalate; diisononylphthalate; diisodecylphthalate; and trioctylphosphate, which is an ester of phosphoric acid.

Other specific examples of fatty ester materials which may be utilized in accordance with this invention include: tri-2-ethylhexylphosphate; di-2-ethylhexylphthalate (DEHP); tri-functional esters such as tri-2-ethylhexyltrimellitate (TEHTM); di-2-ethylhexylmaleate; di-2-ethylhexylazelate; and dibutylphthalate.

Preferably, the fatty ester solution 22 as above described is uniformly dispersed into the whole blood in the form of an emulsion. The emulsion may contain any of the above-described fatty esters emulsified with a sufficient quantity of a hemocompatible surfactant to stabilize the emulsion for a period of time which is at least equal to the time the emulsion is exposed to the blood. Of course, indefinitely stable emulsions are preferred.

Such indefinitely stable emulsions are preferably made by first mixing the fatty ester material with a hemocompatible surfactant or emulsifying agent in the substantial absence of water. After intimate mixing of the fatty ester with the agent, the mixture is added to the water ingredient to form the emulsion.

Any blood-compatible, non-toxic surfactant or emulsifying agent may be used for forming the emulsion, such as polysorbate 80 (as identified in the U.S. Pharmacapoea), which is a mixture of polyoxyethylene ethers of mono oleic ester of sorbitan and sold, for example, as Tween 80 by ICI Americas, Inc. Polyoxyethylene (20) sorbitan monopalmitate can also be used, which is sold by the same company as Tween 40. Pluradot HA410, which is a commercial ester-type emulsifier sold by BASF Wyandotte Corporation, can also be used. Other examples of possible emulsifiers include lecithin and sodium deoxycholate.

The solution 22 may be introduced into the whole blood at the very outset of the storage period and constitute a red blood cell storage solution carried in the container 10 prior to venipuncture. In this embodiment, the storage solution 22 would preferably include, as a part thereof, an anticoagulant solution, such as heperin, citrate, or ethylene diamine tetracetic acid. The storage solution 22 may also include a nutrient added to the anticoagulant, such as citrate phosphate dextrose, with or without adenine (respectively CPD or (CPD-A)); or acid citrate dextrose (ACD).

As the following Examples I, II, IV, and V demonstrate, whole blood into which the solution 22 has been introduced consistently displays substantially lower percentages of crenated red cells throughout the storage period than whole blood into which no solution 22 was added.

For example, and as can be seen in FIG. 3, scanning electron micrographs of the whole blood taken after two weeks of storage clearly reveal that a majority of red cells stored in contact with the solution 22 (FIG. 3c) retain their normal biconcave disc morphology, whereas most red cells stored with no contact with the solution 22 (FIG. 3a) evolve the crenated or spiculated morphology.

Furthermore, and as can be seen in FIG. 4, by the twenty-eighth day of storage, many of the crenated cells in the whole blood stored with no contact with the solution 22 (FIG. 4a) evolve the spherical morphology evidencing irreversible morphological damage. On the other hand, substantially none of the red cells stored in contact with the solution 22 (FIG. 4c) exhibits such severe morphological changes. Indeed, most of the red cells exposed to the solution 22 (FIG. 4c) still retain their normal morphology, even after twenty-eight days of storage.

This marked reduction of red cells exhibiting morphological changes strongly suggests that red blood cells stored in the presence of the solution 22 exhibit an enhanced post-transfusion survival rate.

Alternately, as is shown in phantom lines in FIG. 1, the solution 22 may be added to the whole blood-anticoagulant mixture stored in the container 14 at any time during the storage period. In this embodiment, the solution 22 constitutes an effective blood rejuvenation solution and includes an inorganic salt, such as sodium chloride, potassium chloride and/or sodium phosphate, to be osmotically compatible with whole blood.

As the following Example VI demonstrates, by adding the rejuvenation solution 22 to whole blood which has been stored as long as twenty-one days, an average of one-third of the red blood cells which have undergone morphological changes during the preceeding storage period are rejuvenated and return to their normal forms. The maximum extent of reversal is such that the percentage of normally shaped red blood cells in samples to which the storage solution 22 was dispersed immediately after collection is comparable to samples to which the rejuvenation solution was dispersed after storage of from one to three weeks.

As the following Examples II and III demonstrate, the biological mechanism by which certain fatty esters, such as DEHP, act to prevent hemolysis during red blood cell storage is different from the biological mechanism by which the fatty ester solution 22 of this invention operates. More particularly, at higher concentrations of DEHP (over 150 micrograms per milliliter), little added improvement in the reduction of plasma hemoglobin is observed. Indeed, at progressively higher concentrations (for example, approximately 1500 micrograms per milliliter), the plasma hemoglobin content is observed to rise. However, the ability of the solution 22 which embodies the features of this invention to suppress morphological changes in red cells continues to improve at higher concentrations of the fatty ester.

The following examples are for illustrative purposes and are not intended to limit the invention described herein. It should also be understood that the specific quantitative results obtained in each Example (e.g., the absolute number of normal red cells as compared with the absolute number of crenated or spherical red cells) can and do vary according to the blood physiology of the individual donor involved.

EXAMPLE I

Twenty-one milliliters of whole blood were collected from a healthy donor into a 30 milliliter polypropylene syringe which carried 3.0 milliliters of CPD anticoagulant.

Five milliliter aliquots of the whole blood and anticoagulant mixture were added to sterile polypropylene tubes which, in addition to the whole blood aliquots, included:

TUBE 1 (Buffer Control)

0.5 milliliter of 0.154 M sodium phosphate buffer (pH 7.4)

TUBE 2 (Emulsifier Control)

0.5 milliliter of 0.154 M sodium phosphate buffer (pH 7.4)

1.5 milligrams of a 3:1 (weight to weight) mixture of Tween 80 and Pluradot HA410

TUBE 3 (DEHP Emulsion)

0.5 milliliter of 0.154 M sodium phosphate buffer (pH 7.4)

1.5 milligrams of DEHP emulsified with 1.5 milligrams of the just described Tween 80: Pluradot HA410 mixture The final nominal fatty ester concentration in Tube 3 was 272 micrograms of DEHP per milliliter of whole blood.

Following the addition of the whole blood, Tubes 1, 2, and 3 were capped, gently agitated, and stored at 4° C. for four weeks.

On Days 1, 7, 14, 21, and 28 of the storage period, 0.2 milliliter of whole blood was removed from each tube and examined by scanning electron microscopy. The results of the microscopy are shown in FIGS. 2 through 4.

As can be seen in FIG. 2(a), (b), and (c), the number of crenated and spiculated red cells 18 present after one day of storage was minimal in all three samples.

However, after seven days of storage, a majority of the red blood cells in the Buffer Control and Emulsifier Control samples displayed marked spiculation. In contrast, the bulk of the red blood cells in the DEHP Emulsion retained their biconcave disc morphology.

The differences observed on the seventh day of storage were manifest throughout the remainder of the storage period. As can be seen in FIG. 3(a), (b), and (c), after 14 days of storage, there were essentially no normal red blood cells remaining in the Buffer Control, and only a small number of normal red cells remaining in the Emulsifier Control. In stark contrast, nearly all of the red cells in the DEHP Emulsion displayed their normal biconcave disc morphology.

As can be seen in FIG. 4(a), (b), and (c), after 28 days of storage, many of the crenated cells in the Buffer and Emulsifier Controls had evolved the spherical morphology, evidencing irreversible morphological damage. However, only an occassional spheroechinocyte 20 was observed in the DEHP Emulsion.

This Example provides striking visual proof that the fatty ester solution 22 which embodies the features of the invention can strongly inhibit the spiculation and sphering of red cells during storage.

Red blood cells having the spherical morphology are believed to be rapidly removed by the body from circulation after reinfusion. Thus, the marked reduction of this cell type in whole blood containing the fatty ester solution 22 strongly suggests that red blood cells in such whole blood would exhibit an enhanced post-transfusion survival rate.

EXAMPLE II

A stock fatty ester emulsion was prepared containing, per milliliter of an isotonic sodium phosphate buffer (pH 7.4), 6,000 micrograms of DEHP emulsified with an equal weight of the 3 to 1 (weight to weight) mixture of Tween 80 and Pluradot HA 410.

Utilizing aseptic techniques, aliquots of this stock fatty ester emulsion solution were added to 10.8 milliliter samples of fresh whole blood which had been drawn from a healthy donor into a blood bag which was made of a plastic free of DEHP or similar plasticizer and which contained CPD anticoagulant. A series of test solutions were thus prepared, containing from 50 micrograms of DEHP per milliliter of whole blood to 600 micrograms of DEHP per milliliter of whole blood. An additional volume of 1.2 milliliters of the isotonic phosphate buffer was added to each sample.

A control sample of 10.8 milliliters of blood and 1.2 milliliters of the phosphate buffer was also prepared.

All samples were stored in polypropylene tubes at approximately 4° C.

Aliquots of blood were removed at days 1, 7, 14, 21, 28, and 35 of storage.

Erythrocyte (red cell) morphology was assessed by light microscopy. Samples of the aliquots for examination on glass slides were stained with Wright's solution and examined under an oil immersion objective. The number of crenated (spicule-carrying) red cells in a total cell count of one thousand was determined. No distinction was made between the various forms of crenated cells.

The results of this study are summarized in Table 1 below:

TABLE 1

| DEHP Concentration in the Blood (micrograms/ml.) | Percentage of Red Blood Cells Having Normal Morphology Free of Crenation or Spicules, Observed on the Given Day of Storage | | | | | |
|---|---|---|---|---|---|---|
| | Day 1 | Day 7 | Day 14 | Day 21 | Day 28 | Day 35 |
| 0 | 88 | 10 | 8 | 0 | 0 | 1 |
| 50 | 95 | * | 11 | 1 | 3 | 2 |
| 100 | 98 | 25 | 12 | 3 | 3 | 3 |
| 150 | 98 | 48 | 20 | 7 | 4 | 5 |
| 300 | 98 | 76 | 15 | 16 | 22 | 12 |
| 600 | 99 | 90 | 78 | 46 | 50 | 25 |

*Not observed

Table 1 clearly demonstrates that the percentages of normal red blood cells in whole blood exposed to concentrations of emulsified DEHP equal to or exceeding 150 micrograms per milliliter of whole blood are significantly greater after seven days of storage than in whole blood exposed to lesser concentrations of DEHP or no DEHP at all. Table 1 also clearly demonstrates that the relative differences in the number of normal red blood cells observed after seven days persists throughout the storage period.

Furthermore, Table 1 clearly demonstrates that, when the DEHP concentration is from 300 micrograms per milliliter to 600 micrograms per milliliter, particularly striking increases in the percentages of normal red blood cells present are observed, beginning on the seventh day of storage.

Figure 5:
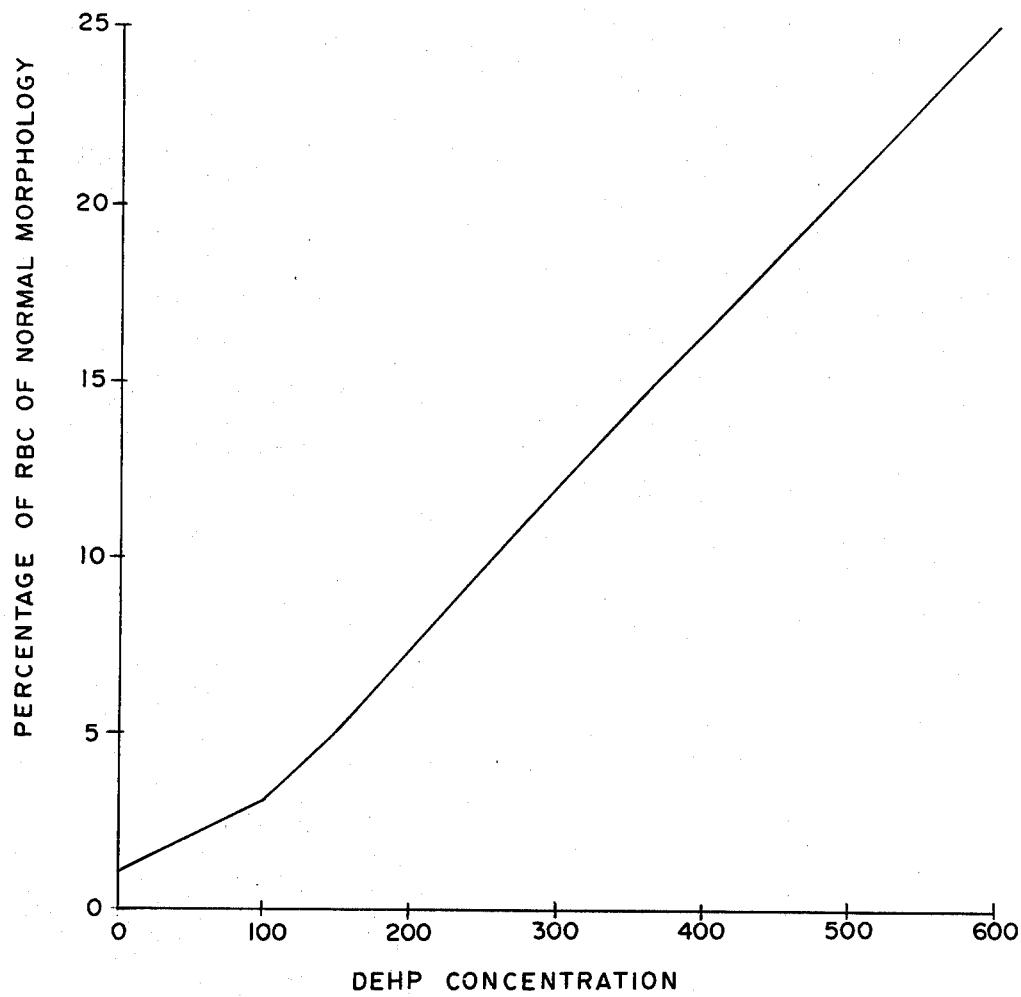
FIG. 5 is a graphical representation of the relationship between concentrations of the fatty ester which embodies the features of the invention and the maintenance of normal red blood cell morphology.

Reference is now made to FIG. 5, which is a graphical representation of the data of Table 1 on the thirty-fifth day of storage. From FIG. 5, it can be seen that the relationship between DEHP concentrations and the preservation of normal red blood cell morphology is nonlinear. The progressively upward trend of this relationship strongly indicates that the maximum concentration of DEHP still capable of effectively preserving normal red blood cell morphology exceeds 600 micrograms per milliliter of whole blood and is thought to be in the neighborhood of 3,000 micrograms per milliliter of whole blood.

Table 1 also clearly demonstrates that, between the first and seventh days of storage, morphological changes in the red cells occur at a much accelerated pace in whole blood exposed to lesser concentrations of DEHP; for example, sharply reducing the percentages of normal red cells from 88% to 10% in whole blood stored without any DEHP, and from 98% to 25% in whole blood exposed to 100 micrograms of DEHP per milliliter of whole blood.

However, Table 1 also demonstrates that exposure to concentrations of DEHP exceeding 150 micrograms per milliliter of whole blood, and preferably exceeding 300 micrograms per milliliter, serves to significantly mitigate morphological changes during this critical period at the outset of storage. For example, 76% of the red cells in whole blood exposed to 300 micrograms of DEHP per milliliter of whole blood remained normal after seven days of storage, and a full 90% remained normal when exposed to a concentration of 600 micrograms of DEHP per milliliter of whole blood.

Such higher concentrations of DEHP are not normally encountered during storage of whole blood, even in conventional DEHP-plasticized polyvinyl chloride plastic bags. This is because the DEHP migrates into the whole blood on a relatively slow basis, and by the seventh day of storage, the DEHP content in whole blood stored in conventional bags is very low. Indeed, it has been observed that, even after 21 days of storage, the extracted DEHP content of whole blood stored in conventional DEHP-plasticized bags is, on the average, 110 micrograms per milliliter, or less.

EXAMPLE III

The same blood samples utilized in Example II to study red blood cell morphology were also utilized to determine the plasma hemoglobin content. The plasma hemoglobin content is a indication of the number of red blood cells which have undergone hemolysis during storage.

The results of the study are summarized in Table 2 below. The plasma hemoglobin concentration (mg%) was determined by a chemical assay using tetramethyl benzidine.

TABLE 2

Plasma Hemoglobin Concentration of Whole Blood Stored at 4° C. with Varying Amounts of Emulsified DEHP

| Nominal DEHP Concentration in the Blood (μg/ml) | Plasma Hemoglobin Concentration (mg %) After Storage | |
|---|---|---|
| | 21 Days | 35 Days |
| 0 | 106 ± 4 | 575 ± 8 |
| 50 | 77 ± 7 | 306 ± 11 |
| 100 | 83 ± 2 | 307 ± 4 |
| 150 | 57 ± 1 | 249 ± 7 |
| 300 | 57 ± 1 | 218 ± 4 |
| 600 | 54 ± 6 | 156 ± 3 |

1. Results are expressed as the average of triplicate determinations ± one standard deviation.

Figure 6:
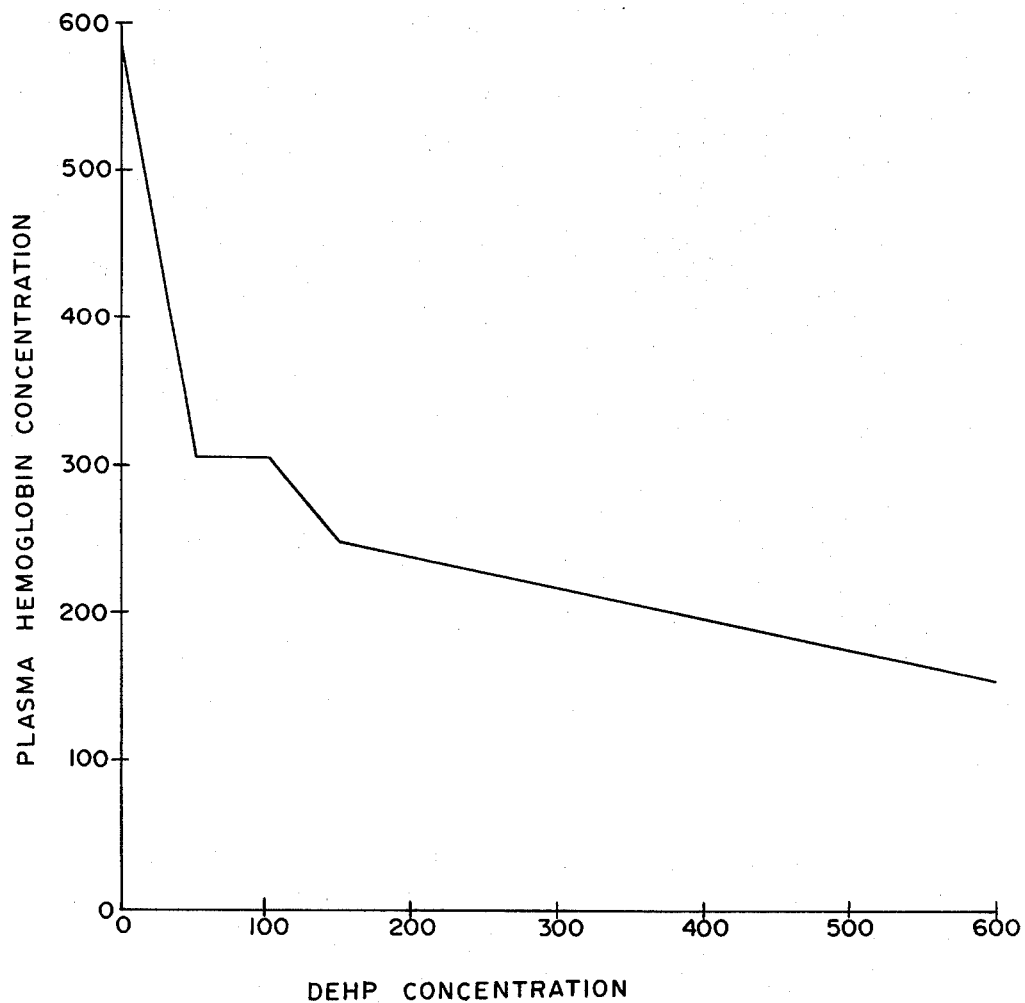
FIG. 6 is a graphical representation of the relationship between concentrations of DEHP and plasma hemoglobin accumulation in whole blood.

Reference is made to FIG. 6, which is a graphical representation of the data of Table 2 on the thirty-fifth day of storage. From FIG. 6, it is apparent that the increase in DEHP concentration up to 600 micrograms per milliliter of whole blood is correlated with a decrease in plasma hemoglobin accumulation. However, as FIG. 6 demonstrates, the relationship is highly non-linear, with the reduction in plasma hemoglobin accumulation effectively approaching a limiting value of approximately 150 mg% hemoglobin at the higher DEHP concentrations.

In another experiment, and utilizing a healthy donor different than the one utilized in Example II, one unit of whole blood was drawn into a DEHP-free container carrying CPD anticoagulant. The blood was subdivided into separate 58 milliliter fractions. Into separate 58 milliliter fractions, 0.2, 0.6, 2.0 or 6.0 milliliters of a DEHP emulsion were added, along with enough phosphate buffer to make the volume of added solution equal to 6.0 milliliter in each case. The nominal DEHP concentrations resulting were 50, 150, 500, and 1500 micrograms per milliliter.

The plasma hemoglobin values (mg%) were calculated for each sample on days 7, 14, 21, 28, and 35 of storage, utilizing the same chemical assay procedure as just described. The plasma hemoglobin value for a whole blood/buffer control sample was also determined for each of the days.

Figure 7:
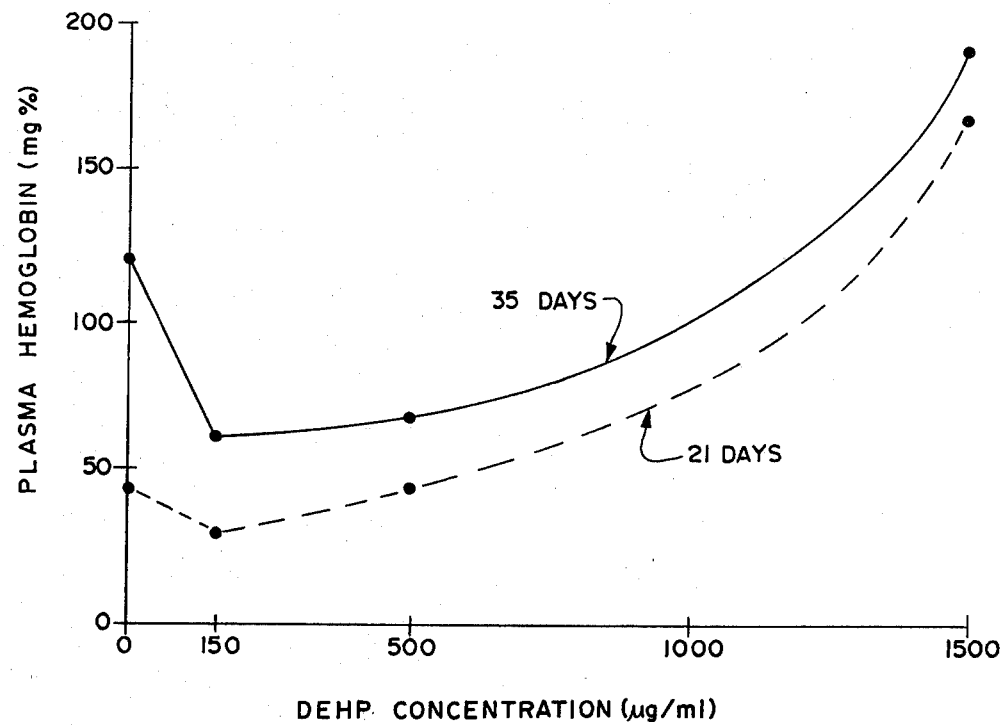
FIG. 7 is another graphical representation of the relationship between concentrations of DEHP and plasma hemoglobin concentration of whole blood.

The results are summarized in Table 3 and in FIG. 7.

Table 3 and FIG. 7 demonstrate generally comparable plasma hemoglobin concentrations in 35 day old blood samples containing 50 to 500 micrograms of DEHP per milliliter of whole blood, while samples containing 0 micrograms (i.e., the Buffer Control) or 1500 micrograms of DEHP per milliliter of whole blood exhibit a markedly higher plasma hemoglobin content.

appear that the mechanism of fatty esters, such as DEHP, to prevent the rupture of red blood cells upon storage, and the consequent rise in plasma hemoglobin, is different from the mechanism which causes higher concentrations of DEHP to reduce morphological changes in the red blood cells on storage. As Table 3 and FIG. 7 demonstrate, at concentrations over 150 micrograms DEHP per milliliter of whole blood, little added improvement in the reduction of plasma hemoglobin during storage is found. In fact, the data demonstrates that, at the higher DEHP concentrations, the plasma hemoglobin content begins to rise. To the contrary, and as Table 1 and FIG. 5 demonstrate, the reduction of morphological changes in blood cells is observed to continue to progressively improve with ever-increasing quantities of the fatty ester, such as DEHP, and no lessening or reversal of the effect is expected to be observed up to at least 3,000 micrograms of the fatty ester per milliliter of whole blood.

EXAMPLE IV

A stock solution was prepared of 33.75 micrograms of DEHP [emulsified with an equal weight of 3:1 (weight:weight) of Tween 80: Pluradot HA 410] per milliliter of isotonic sodium phosphate buffer (pH 7.4). A control solution containing 33.75 micrograms of the emulsifier per milliliter of the phosphate buffer, without any DEHP, was also prepared.

Four units of whole blood were drawn from a healthy donor into DEHP-free containers carrying CPD anticoagulant. The whole blood was divided into four, 200 milliliter samples.

Two milliliters of the DEHP emulsion were dispersed into each of two of the samples for a resulting nominal concentration of 340 micrograms DEHP per milliliter of whole blood. Two milliliters of the emulsifier control solution were dispersed into each of the remaining samples. The samples were all placed into a refrigerator maintained at 4° C.

At days 1, 7, 14, 21, 28, and 35 of storage, the red blood cell morphology was analyzed by light microscopy.

The results are summarized in Table 4.

Table 4 clearly demonstrates the consistent and marked improvement in red blood cell morphology which occurs from the addition of the fatty ester emulsion solution. The enhanced preservation of normal red cell morphology persists throughout the storage period. By the thirty-fifth day of storage, over three times as many normal biconcave cells are present in whole blood exposed to the fatty ester than whole blood exposed only to the emulsifier.

Furthermore, the number of irreversibly damaged

TABLE 3

| Sample | PLASMA HEMOGLOBIN VALUES (mg %)[1] | | |
|---|---|---|---|
| | Day 21 | Day 28 | Day 35 |
| Buffer Control | 43.2 ± 12.3 (2) | 60.3 ± 16.1 (3) | 119.7 ± 18.3 (3) |
| 50 μg/ml DEHP | 38.8 ± 4.1 (3) | 48.1 ± 7.7 (3) | 71.5 ± 1.3 (3) |
| 150 μg/ml DEHP | 26.7 ± 2.6 (3) | 37.5 ± 2.4 (3) | 61.6 ± 8.1 (3) |
| 500 μg/ml DEHP | 41.3 ± 10.8 (3) | 75.1 ± 17.6 (3) | 67.4 ± 4.0 (3) |
| 1500 μg/ml DEHP | 167.3 ± 13.0 (3) | 179.3 ± 21.9 (3) | 192.7 ± 57.3 (3) |

[1]Results are averages ± one standard deviation. Values in parenthesis are the number of samples included in the average. All samples are assayed in triplicate.

On the basis of the above data, and without wishing to be bound at this point to any specific theoretical explanation of the mechanism taking place, it would spherical cells is three-fold lower in blood with the fatty ester emulsion solution than in blood without the solution.

TABLE 4

Red Blood Cell Morphology in Whole Blood Stored with and without Emulsified DEHP

| SAMPLE | PERCENTAGE OF CELL TYPES[1] | | | | | | | | |
|---|---|---|---|---|---|---|---|---|---|
| | DAY 1 | | | DAY 7 | | | DAY 14 | | |
| | N | C | S | N | C | S | N | C | S |
| A Emulsion | 88 | 12 | 0 | 69 | 31 | 0 | 38 | 62 | 0 |
| A DEHP | 97 | 3 | 0 | 96 | 3 | 1 | 93 | 7 | 0 |
| B Emulsion | 71 | 29 | 0 | 48 | 52 | 0 | 24 | 74 | 2 |
| B DEHP | 96 | 4 | 0 | 90 | 10 | 0 | 78 | 22 | 0 |
| C Emulsion | 80 | 20 | 0 | 64 | 36 | 1 | 34 | 66 | 0 |
| C DEHP | 97 | 4 | 0 | 94 | 6 | 0 | 90 | 10 | 0 |
| D Emulsion | 91 | 9 | 0 | 52 | 48 | 0 | 37 | 63 | 0 |
| D DEHP | 97 | 3 | 0 | 93 | 7 | 0 | 78 | 22 | 0 |
| Average[2] | | | | | | | | | |
| Emulsion | 83 ± 9 | 18 ± 9 | 0 ± 0 | 58 ± 10 | 42 ± 10 | 0 ± 1 | 33 ± 6 | 66 ± 5 | 1 ± 1 |
| DEHP | 97 ± 1 | 4 ± 1 | 0 ± 0 | 93 ± 3 | 7 ± 3 | 0 ± 1 | 85 ± 8 | 15 ± 8 | 0 ± 0 |

| SAMPLE | PERCENTAGE OF CELL TYPES[1] | | | | | | | | |
|---|---|---|---|---|---|---|---|---|---|
| | DAY 21 | | | DAY 28 | | | DAY 35 | | |
| | N | C | S | N | C | S | N | C | S |
| A Emulsion | 35 | 64 | 1 | 28 | 67 | 6 | 21 | 56 | 24 |
| A DEHP | 91 | 8 | 1 | 75 | 24 | 1 | 66 | 27 | 7 |
| B Emulsion | 12 | 83 | 5 | 14 | 71 | 15 | 12 | 62 | 26 |
| B DEHP | 72 | 27 | 2 | 61 | 35 | 5 | 46 | 48 | 7 |
| C Emulsion | 17 | 81 | 2 | 10 | 84 | 6 | 9 | 69 | 21 |
| C DEHP | 85 | 15 | 0 | 62 | 38 | 0 | 44 | 48 | 8 |
| D Emulsion | 28 | 68 | 4 | 26 | 73 | 1 | 16 | 78 | 6 |
| D DEHP | 80 | 19 | 1 | 69 | 30 | 1 | 55 | 43 | 2 |
| Average[2] | | | | | | | | | |
| Emulsion | 23 ± 10 | 74 ± 9 | 3 ± 2 | 20 ± 9 | 74 ± 7 | 7 ± 6 | 15 ± 5 | 66 ± 9 | 19 ± 9 |
| DEHP | 82 ± 8 | 17 ± 8 | 1 ± 1 | 67 ± 7 | 32 ± 6 | 2 ± 2 | 53 ± 10 | 42 ± 10 | 6 ± 3 |

[1]N = Normal Morphology, C = Crenated, S = Spherical.
[2]Results are expressed as the average of the four samples ± one standard deviation.

EXAMPLE V

Separate emulsions were prepared of 30 milligrams each of the following fatty esters: DEHP; tri-(2-ethylhexyl) phosphate (TOF); diisononyl phthalate (DINP); diisodecyl phthalate (DIDP); dihexyl phthalate (DHP); and TEHTM. In each emulsion, 30 milligrams of the fatty ester were mixed with 30 milligrams of 3:1 (weight: weight) Tween 80: Pluradot HA 410. Each emulsion was suspended in ten milliliters of 0.154 M sodium phosphate buffer (pH 7.4).

Emulsifier control solutions were also prepared by mechanical agitation of 30 milligrams of the Tween 80: Pluradot HA 410 mixture with 10 milliliters of the sodium phosphate buffer.

Nine milliliter aliquots of whole blood drawn from a healthy donor were prepared. The above emulsions were added to separate whole blood aliquots to achieve a nominal concentration of 300 micrograms of fatty ester per milliliter of whole blood. The emulsifier control solution and the phosphate buffer were also added to the remaining aliquots.

The samples were stored at 4° C. for five weeks. After 21 and 35 days of storage, the red blood morphology was assessed in each sample.

The results are summarized in Table 5.

TABLE 4

Morphology of Red Blood Cells in Whole Blood Stored at 4° C. with Different Plasticizer Emulsions

| Experiment | Additions | Average % Cell Type[1] | | | | | |
|---|---|---|---|---|---|---|---|
| | | Day 21 | | | Day 35 | | |
| | | Normal | Crenated | Spherical | Normal | Crenated | Spherical |
| 1 | Buffer Control | 4 ± 2 | 94 ± 2 | 3 ± 1 | 1 ± 1 | 85 ± 1 | 14 ± 1 |
| | Emulsifier Control | 1 ± 1 | 96 ± 1 | 2 ± 1 | 2 ± 1 | 92 ± 3 | 6 ± 3 |
| | DEHP Emulsion | 53 ± 12 | 47 ± 11 | 1 ± 1 | 26 ± 6 | 72 ± 7 | 3 ± 3 |
| | DINP Emulsion | 30 ± 10 | 69 ± 10 | 0 ± 1 | 19 ± 8 | 81 ± 8 | 1 ± 1 |
| | DIDP Emulsion | 29 ± 5 | 71 ± 5 | 1 ± 1 | 19 ± 5 | 78 ± 4 | 3 ± 3 |
| | TOF Emulsion | 78 ± 4 | 22 ± 4 | 0 ± 0 | 66 ± 9 | 33 ± 10 | 1 ± 1 |
| 2 | Buffer Cntrol | 10 ± 5 | 83 ± 4 | 6 ± 1 | 4 ± 2 | 79 ± 6 | 17 ± 4 |
| | Emulsifier Control | 14 ± 10 | 83 ± 10 | 3 ± 1 | 8 ± 8 | 78 ± 5 | 14 ± 7 |
| | DEHP Emulsion | 73 ± 9 | 27 ± 9 | 1 ± 1 | 68 ± 1 | 29 ± 2 | 3 ± 1 |
| | DHP Emulsion | 33 ± 1 | 66 ± 3 | 1 ± 2 | 28 ± 13 | 67 ± 10 | 5 ± 4 |
| | TEHTM Emulsion | 65 ± 11 | 35 ± 11 | 1 ± 1 | 53 ± 4 | 44 ± 5 | 3 ± 1 |

[1]Results are expressed as the average of three samples ± one standard deviation.

Table 5 clearly demonstrates that all of the fatty esters utilized inhibit the rate of red blood cell crenation. In addition, the formation of spherical cells was reduced in blood containing the fatty esters as compared to the controls.

The order of potency of each of the fatty esters with respect to the ability to preserve normal red blood cell morphology decreases in the following order (1) TOF (most effective); (2) DEHP; (3) TEHTM; (4) DINP or DIDP; and (5) DHP (least effective).

However, with even the least effective fatty ester tested (DHP), the number of normally shaped red cells in blood stored for 35 days was over three times that in the buffer or emulsifier controls.

Table 5 clearly indicates that the various fatty esters as heretofore described exhibit the ability to enhance the preservation of normal red blood cell morphology.

EXAMPLE VI

Six units of whole blood were collected from different healthy human donors into multiple blood bags having two connected transfer packs. The blood bags were made of a plastic material free of phthalate-type plasticizers and containing CPD anticoagulant. Duplicate 200 milliliter volumes of blood from each unit were drained into the separate transfer packs of the multiple bag systems.

Added to one transfer pack from each unit was 2.0 milliliter of isotonic sodium phosphate buffer at pH 7.4. Added to the remaining transfer packs of each unit was 2.0 milliliter of a phosphate buffer containing a concentration of 30 milligrams per milliliter of DEHP emulsified with 30 milligrams per milliliter of a 3:1 (weight:weight) mixture of Tween 80: Pluradot HA 410 emulsifier. The DEHP emulsion was prepared as in Example I. The resulting nominal concentration was 300 micrograms of DEHP per milliliter of whole blood.

After thorough mixing, the transfer packs were placed into a refrigerator maintained at 4° C. Each of the transfer packs were sampled after various days of storage.

On the seventh day of storage, duplicate 10 milliliter aliquots of blood were removed from each of two of the transfer packs containing the phosphate buffer, but without DEHP. These aliquots were placed into four separate, sterile, polypropylene tubes. To one of the aliquots of blood from each transfer pack was added 0.1 milliliter of the 30 milligram per milliliter DEHP emulsion to again yield a final DEHP concentration in the whole blood of 300 micrograms per milliliter. Added to the remaining aliquots was 0.1 milliliter of phosphate buffer solution. These samples were mixed and also stored at 4° C.

The same procedure was also followed on days 14 and 21 of the experiment.

Red blood cell morphology of various samples was analyzed by light microscopy at days 1, 7, 8, 11, 14, 15, 18, 21, 22, 25, 28, and 35 of storage. The results are as indicated in Table 6a and 6b, with the blank areas in the Table indicating that no data was taken for the particular conditions indicated. As in Table 4, in the respective columns representing each day of storage, the letter N stands for the percentage of normal red cells observed; the letter C represents the percentage of crenated cells observed; and the letter S represents the percentage of spherical cells observed.

TABLE 6a

PERCENTAGE OF RED BLOOD CELL TYPES IN WHOLE BLOOD MAINTAINED AT 4° C. WITH AND WITHOUT EMULSIFIED DEHP ADDED AT DIFFERENT TIMES DURING STORAGE

| SAMPLE | ADDITIVE | DAY OF ADDITION | 1 N | 1 C | 1 S | 7 N | 7 C | 7 S | 8 N | 8 C | 8 S | 11 N | 11 C | 11 S | 14 N | 14 C | 14 S | 15 N | 15 C | 15 S |
|---|---|---|---|---|---|---|---|---|---|---|---|---|---|---|---|---|---|---|---|---|
| A | Buffer only | 0 | 91 | 8 | 0 | 62 | 38 | 0 | | | | | | | 26 | 69 | 5 | | | |
|   | DEHP | 0 | 99 | 1 | 0 | 98 | 2 | 0 | | | | | | | 84 | 16 | 0 | | | |
|   | Buffer only | 7 | | | | 57 | 43 | 0 | 63 | 37 | 0 | 39 | 61 | 0 | 40 | 57 | 2 | | | |
|   | DEHP | 7 | | | | 65 | 35 | 0 | 80 | 20 | 0 | 85 | 15 | 0 | 86 | 14 | 0 | | | |
| B | Buffer only | 0 | 86 | 14 | 0 | 37 | 62 | 0 | | | | | | | 12 | 87 | 0 | | | |
|   | DEHP | 0 | 98 | 2 | 0 | 87 | 13 | 0 | | | | | | | 74 | 25 | 1 | | | |
|   | Buffer only | 7 | | | | 31 | 70 | 0 | 33 | 67 | 0 | 29 | 70 | 0 | 28 | 72 | 0 | | | |
|   | DEHP | 7 | | | | 36 | 64 | 0 | 58 | 42 | 0 | 63 | 37 | 0 | 70 | 30 | 0 | | | |
| C | Buffer only | 0 | 91 | 9 | 0 | 40 | 60 | 0 | | | | | | | 20 | 79 | 1 | | | |
|   | DEHP | 0 | 99 | 1 | 0 | 90 | 10 | 0 | | | | | | | 66 | 33 | 0 | | | |
|   | Buffer only | 14 | | | | | | | | | | | | | 22 | 78 | 0 | 27 | 72 | 0 |
|   | DEHP | 14 | | | | | | | | | | | | | 19 | 79 | 1 | 43 | 57 | 0 |
| D | Buffer only | 0 | 92 | 8 | 0 | 30 | 70 | 0 | | | | | | | 19 | 77 | 4 | | | |
|   | DEHP | 0 | 96 | 4 | 0 | 88 | 12 | 0 | | | | | | | 78 | 21 | 1 | | | |
|   | Buffer Only | 14 | | | | | | | | | | | | 19 | 78 | 3 | 24 | 74 | 2 | |
|   | DEHP | 14 | | | | | | | | | | | | | 25 | 74 | 1 | 40 | 60 | 1 |
| E | Buffer only | 0 | 78 | 22 | 0 | 24 | 76 | 0 | | | | | | | 5 | 94 | 1 | | | |
|   | DEHP | 0 | 97 | 3 | 0 | 90 | 10 | 0 | | | | | | | 77 | 23 | 0 | | | |
|   | Buffer only | 21 | | | | | | | | | | | | | | | | | | |
|   | DEHP | 21 | | | | | | | | | | | | | | | | | | |
| F | Buffer only | 0 | 95 | 5 | 0 | 41 | 59 | 0 | | | | | | | 26 | 73 | 0 | | | |
|   | DEHP | 0 | 99 | 1 | 0 | 93 | 7 | 0 | | | | | | | 91 | 9 | 0 | | | |
|   | Buffer only | 21 | | | | | | | | | | | | | | | | | | |
|   | DEHP | 21 | | | | | | | | | | | | | | | | | | |

TABLE 6b

PERCENTAGE OF RED CELL TYPES IN WHOLE BLOOD MAINTAINED AT 4° C. WITH AND WITHOUT EMULSIFIED DEHP ADDED AT DIFFERENT TIMES DURING STORAGE

| SAMPLE | ADDITIVE | DAY OF ADDITION | 18 N | 18 C | 18 S | 21 N | 21 C | 21 S | 22 N | 22 C | 22 S | 25 N | 25 C | 25 S | 28 N | 28 C | 28 S | 35 N | 35 C | 35 S |
|---|---|---|---|---|---|---|---|---|---|---|---|---|---|---|---|---|---|---|---|---|
| A | Buffer only | 0 | | | | 16 | 81 | 3 | | | | | | | 13 | 78 | 9 | 4 | 79 | 16 |
|   | DEHP | 0 | | | | 85 | 15 | 0 | | | | | | | 58 | 42 | 1 | 40 | 57 | 3 |
|   | Buffer only | 7 | | | | 24 | 76 | 0 | | | | | | | 15 | 82 | 3 | 6 | 84 | 10 |
|   | DEHP | 7 | | | | 95 | 5 | 0 | | | | | | | 87 | 13 | 0 | 63 | 36 | 1 |
| B | Buffer only | 0 | | | | 13 | 76 | 11 | | | | | | | 3 | 88 | 9 | 3 | 82 | 15 |
|   | DEHP | 0 | | | | 62 | 38 | 0 | | | | | | | 44 | 55 | 1 | 28 | 64 | 8 |
|   | Buffer only | 7 | | | | 22 | 77 | 1 | | | | | | | 9 | 85 | 5 | 5 | 89 | 6 |
|   | DEHP | 7 | | | | 83 | 16 | 0 | | | | | | | 67 | 32 | 0 | 45 | 52 | 3 |

TABLE 6b-continued
PERCENTAGE OF RED CELL TYPES IN WHOLE BLOOD MAINTAINED AT 4° C.
WITH AND WITHOUT EMULSIFIED DEHP ADDED AT DIFFERENT TIMES DURING STORAGE

| SAMPLE | ADDITIVE | DAY OF ADDITION | 18 N | 18 C | 18 S | 21 N | 21 C | 21 S | 22 N | 22 C | 22 S | 25 N | 25 C | 25 S | 28 N | 28 C | 28 S | 35 N | 35 C | 35 S |
|---|---|---|---|---|---|---|---|---|---|---|---|---|---|---|---|---|---|---|---|---|
| C | Buffer only | 0 | | | | 7 | 89 | 4 | | | | | | | 2 | 87 | 11 | 2 | 78 | 20 |
| | DEHP | 0 | | | | 67 | 32 | 1 | | | | | | | 39 | 59 | 3 | 28 | 66 | 5 |
| | Buffer only | 14 | 10 | 88 | 2 | 17 | 81 | 2 | | | | | | | 4 | 88 | 8 | 2 | 83 | 16 |
| | DEHP | 14 | 54 | 45 | 0 | 69 | 30 | 1 | | | | | | | 64 | 35 | 1 | 40 | 57 | 3 |
| D | Buffer only | 0 | | | | 6 | 84 | 10 | | | | | | | 7 | 80 | 13 | 5 | 67 | 28 |
| | DEHP | 0 | | | | 62 | 34 | 4 | | | | | | | 47 | 52 | 1 | 41 | 50 | 9 |
| | Buffer only | 14 | 16 | 81 | 3 | 18 | 75 | 7 | | | | | | | 6 | 84 | 10 | 5 | 73 | 22 |
| | DEHP | 14 | 51 | 48 | 1 | 66 | 29 | 4 | | | | | | | 59 | 37 | 4 | 42 | 47 | 10 |
| E | Buffer only | 0 | | | | 4 | 91 | 4 | | | | | | | 2 | 94 | 4 | 1 | 89 | 10 |
| | DEHP | 0 | | | | 62 | 37 | 1 | | | | | | | 53 | 45 | 2 | 46 | 49 | 5 |
| | Buffer only | 21 | | | | 17 | 82 | 1 | 10 | 87 | 3 | 7 | 80 | 14 | 4 | 93 | 3 | 1 | 89 | 10 |
| | DEHP | 21 | | | | 31 | 68 | 1 | 55 | 44 | 1 | 52 | 45 | 3 | 41 | 57 | 2 | 43 | 53 | 4 |
| F | Buffer only | 0 | | | | 20 | 77 | 3 | | | | | | | 11 | 78 | 11 | 4 | 83 | 12 |
| | DEHP | 0 | | | | 82 | 18 | 1 | | | | | | | 67 | 32 | 1 | 56 | 41 | 3 |
| | Buffer only | 21 | | | | 24 | 75 | 1 | 25 | 74 | 1 | 10 | 89 | 2 | 8 | 87 | 5 | 7 | 83 | 10 |
| | DEHP | 21 | | | | 41 | 59 | 6 | 74 | 26 | 0 | 64 | 34 | 1 | 69 | 29 | 2 | 56 | 36 | 7 |

Table 6a and 6b demonstrates that the addition of 300 micrograms of emulsified DEHP per milliliter of whole blood after 7, 14, or 21 days of storage results in a reversal of crenation in an average of one-third of the red blood cells present.

The reversal process is evident within a day after the introduction of the DEHP and continues for approximately two weeks in whole blood to which the DEHP is added after seven days of storage.

When DEHP is added to whole blood stored for 14 days, the maximum reversal occurs approximately one week later, while reversal peaks on the twenty-second day when the DEHP is added on the twenty-first day.

After the maximum reversal was achieved, the percentage of normal red blood cells declines at a rate which is similar in samples containing DEHP added immediately after collection or at different times during storage.

No marked reversal of red blood cell crenation was observed when phosphate buffer alone was added to the stored blood.

Various of the features of the invention are set forth in the following claims.

I claim:

1. An additive solution for preserving normal red blood cell morphology during whole blood storage, said solution comprising
   a fatty ester including at least two ester linkages comprising fatty hydrocarbon groups of about four to twelve carbon atoms each, said fatty ester being present in a concentration of between 150 and 3,000 micrograms per milliliter of whole blood.

2. An additive solution according to claim 1 wherein said fatty ester is present in a concentration of between 250 and 500 micrograms per milliliter of whole blood.

3. An additive solution according to claim 1 or 2 wherein said fatty ester is in the form of an emulsion.

4. An additive solution according to claim 1 or 2 and further including, as part of said solution, an anticoagulant.

5. An additive solution according to claim 4 and further including, as part of said solution, a nutrient for the whole blood.

6. An additive solution for rejuvenating red blood cells which have undergone morphological changes during whole blood storage, said solution comprising
   a fatty ester including at least two ester linkages comprising fatty hydrocarbon groups of about four to twelve carbon atoms each, said fatty ester being present in a concentration of between 150 and 3,000 micrograms per milliliter of whole blood.

7. An additive solution according to claim 6 wherein said fatty ester is present in a concentration of between 250 and 500 micrograms per milliliter of whole blood.

8. An additive solution according to claim 6 or 7 wherein said fatty ester is in the form of an emulsion.

9. A solution according to claim 1 or 6 wherein said fatty ester is a phosphate ester.

10. A solution according to claim 9 wherein said phosphate ester has three alkyl groups.

11. A solution according to claim 1 or 6 wherein said fatty ester is a phthalate diester.

12. A solution according to claim 1 or 6 wherein said fatty hydrocarbon groups are alkyl.

13. A solution according to claim 1 or 6 wherein said fatty hydrocarbon groups each contain from seven to ten carbon atoms.

14. A solution according to claim 1 or 6 wherein said fatty ester comprises a pair of ester linkages bound to a highly mobile hydrocarbon chain.

15. A solution according to claim 14 wherein said highly mobile hydrocarbon chain is a linear alkylene chain.

16. A solution according to claim 15 wherein said linear alkylene chain contains no more than eight carbon atoms excluding the ester linkage carbon atoms.

17. A solution according to claim 1 or 6 wherein said ester linkages are bonded to adjacent carbon atoms.

18. A solution according to claim 1 or 6 wherein said fatty ester is a dioctylphthalate.

19. A solution according to claim 18 wherein said fatty ester is di-2-ethylhexylphthalate.

20. A whole blood storage system comprising
   a container having an interior for receiving whole blood for storage,
   a solution carried within said interior and including a fatty ester including at least two ester linkages comprising fatty hydrocarbon groups of about four to twelve carbon atoms each, said fatty ester being present in a concentration of between 150 and 3,000 micrograms per milliliter of whole blood stored within said container.

21. A whole blood storage system according to claim 20
wherein said fatty ester is present in a concentration of between 250 and 500 micrograms per milliliter of whole blood.

22. A whole blood storage system according to claim 20 or 21
wherein said fatty ester is in the form of an emulsion.

23. A whole blood storage system according to claim 20 or 21
wherein said solution further includes, as a part thereof, an anticoagulant.

24. A whole blood storage system according to claim 23
wherein said solution further includes, as a part thereof, a nutrient for the whole blood.

25. A whole blood storage system according to claim 24
wherein said container includes
a donor tube having an end attached in flow communication with said interior and an opposite end, and
a phlebotomy needle attached in flow communication with said opposite end.

26. A method for storing whole blood so as to preserve normal red blood morphology during the storage period, said method comprising the step of
introducing for each milliliter of whole blood present between 150 and 3,000 micrograms of a fatty ester containing at least two ester linkages comprising fatty hydrocarbon groups of four to twelve carbon atoms each.

27. A method according to claim 26
and further including, prior to said fatty ester introduction step, the step of emulsifying the fatty ester.

28. A method according to claim 26 or 27
wherein said fatty ester introduction step includes introducing for each milliliter of whole blood present between 250 and 500 micrograms per milliliter the fatty ester.

29. A method according to claim 26 or 27
wherein said fatty ester introduction step includes introducing the fatty ester at the outset of the storage period.

30. A method according to claim 26 or 27
wherein said fatty ester introduction step includes introducing the fatty ester at any time after the outset of the storage period.

* * * * *